United States Patent
Fehre et al.

(10) Patent No.: US 9,706,629 B2
(45) Date of Patent: Jul. 11, 2017

(54) X-RAY APPARATUS WITH VOLTAGE GENERATOR COMPONENT DISPOSED AT THE SAME END OF A C-ARM AS A DETECTOR

(71) Applicant: SIEMENS AKTIENGESELLSCHAFT, Munich (DE)

(72) Inventors: Jens Fehre, Hausen (DE); Udo Heinze, Erlangen (DE); Ralf Nanke, Neunkirchen am Brand (DE)

(73) Assignee: Siemens Aktiengesellschaft, Munich (DE)

( * ) Notice: Subject to any disclaimer, the term of this patent is extended or adjusted under 35 U.S.C. 154(b) by 16 days.

(21) Appl. No.: 14/704,068

(22) Filed: May 5, 2015

(65) Prior Publication Data
US 2015/0319831 A1 Nov. 5, 2015

(30) Foreign Application Priority Data
May 5, 2014 (DE) .......................... 10 2014 208 345

(51) Int. Cl.
*H05G 1/02* (2006.01)
*H05G 1/10* (2006.01)
*G01N 23/04* (2006.01)
*A61B 6/00* (2006.01)
*H05G 1/12* (2006.01)
*H01J 35/26* (2006.01)

(52) U.S. Cl.
CPC ............. *H05G 1/10* (2013.01); *A61B 6/4441* (2013.01); *A61B 6/56* (2013.01); *G01N 23/04* (2013.01); *H05G 1/02* (2013.01); *H05G 1/12* (2013.01); *H01J 35/26* (2013.01)

(58) Field of Classification Search
CPC .... H05G 1/10; A61B 6/42; A61B 6/44; A61B 6/4435; A61B 6/4441
USPC .................................................. 378/197, 198
See application file for complete search history.

(56) References Cited

U.S. PATENT DOCUMENTS

| 6,789,941 | B1 * | 9/2004 | Grady .................. A61B 6/4233 378/196 |
| 7,887,236 | B2 | 2/2011 | Dehler et al. |
| 2006/0233297 | A1 | 10/2006 | Ishiyama |

(Continued)

FOREIGN PATENT DOCUMENTS

| DE | 69420936 T2 | 4/2000 |
| DE | 102007026677 A1 | 12/2008 |

(Continued)

*Primary Examiner* — Jason McCormack
(74) *Attorney, Agent, or Firm* — Laurence Greenberg; Werner Stemer; Ralph Locher

(57) ABSTRACT

An x-ray apparatus is configured with a C-arm frame. At one end of the C-arm frame an x-ray source is arranged and at the other end of which a detector for recording radiation emitted by the x-ray source is arranged. A voltage generator is provided for supplying a voltage to the x-ray source. At least one component of the voltage generator and the x-ray source are arranged separately from one another. The at least one component of the voltage generator is positioned at the same end of the C-arm frame at which the detector is arranged, as a result of which a weight equalization can be implemented in a simpler manner.

8 Claims, 4 Drawing Sheets

(56) References Cited

U.S. PATENT DOCUMENTS

| | | | |
|---|---|---|---|
| 2009/0010393 A1* | 1/2009 | Klinkowstein | H05G 1/10 378/140 |
| 2012/0243667 A1* | 9/2012 | Walters | A61B 6/4405 378/206 |
| 2013/0170615 A1* | 7/2013 | Wei | G01T 1/24 378/62 |

FOREIGN PATENT DOCUMENTS

| | | | | |
|---|---|---|---|---|
| DE | 102009018283 A1 | 12/2010 | | |
| DE | 102010028511 A1 | 11/2011 | | |
| DE | 102009018283 B4 * | 11/2014 | | A61B 6/4441 |

* cited by examiner

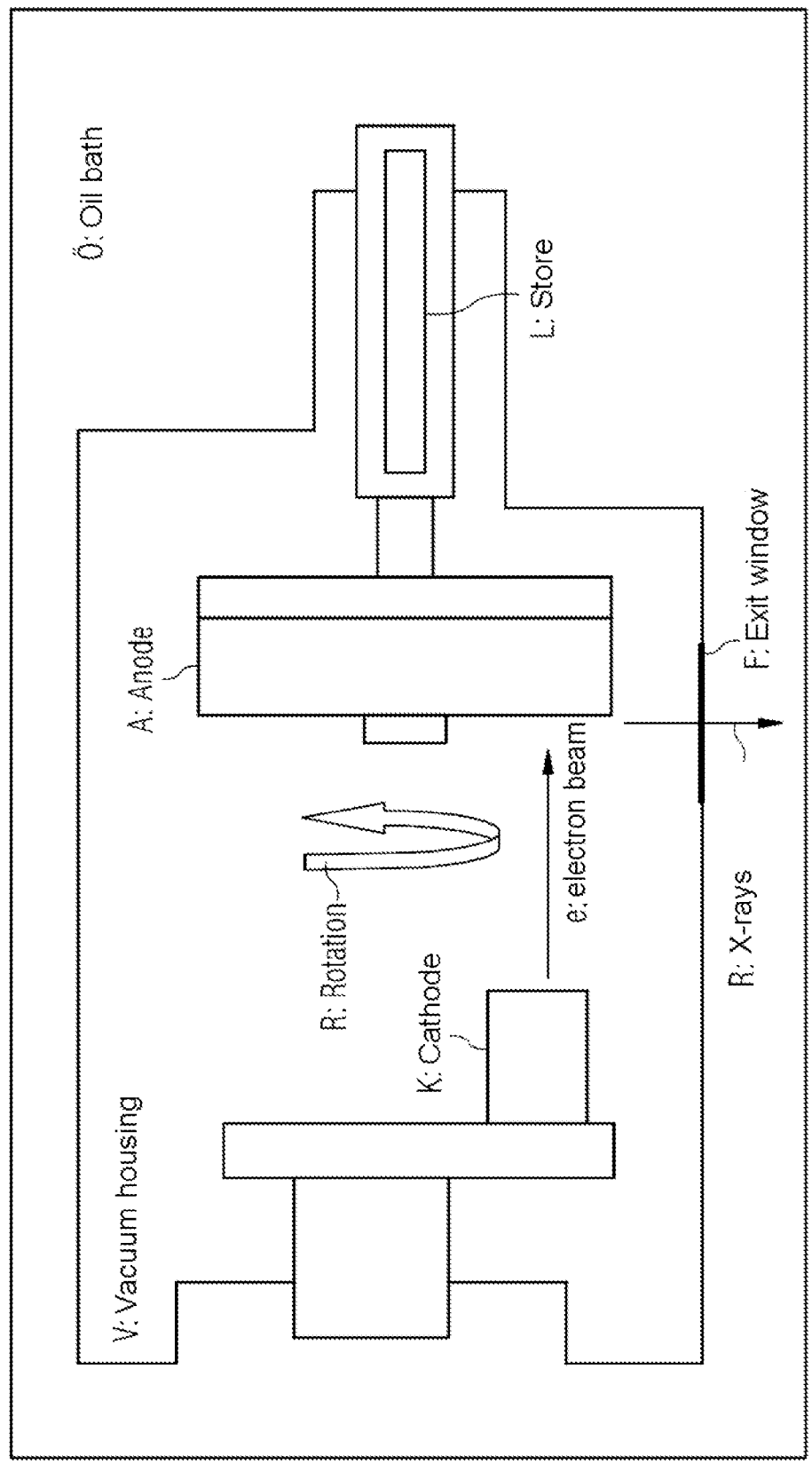

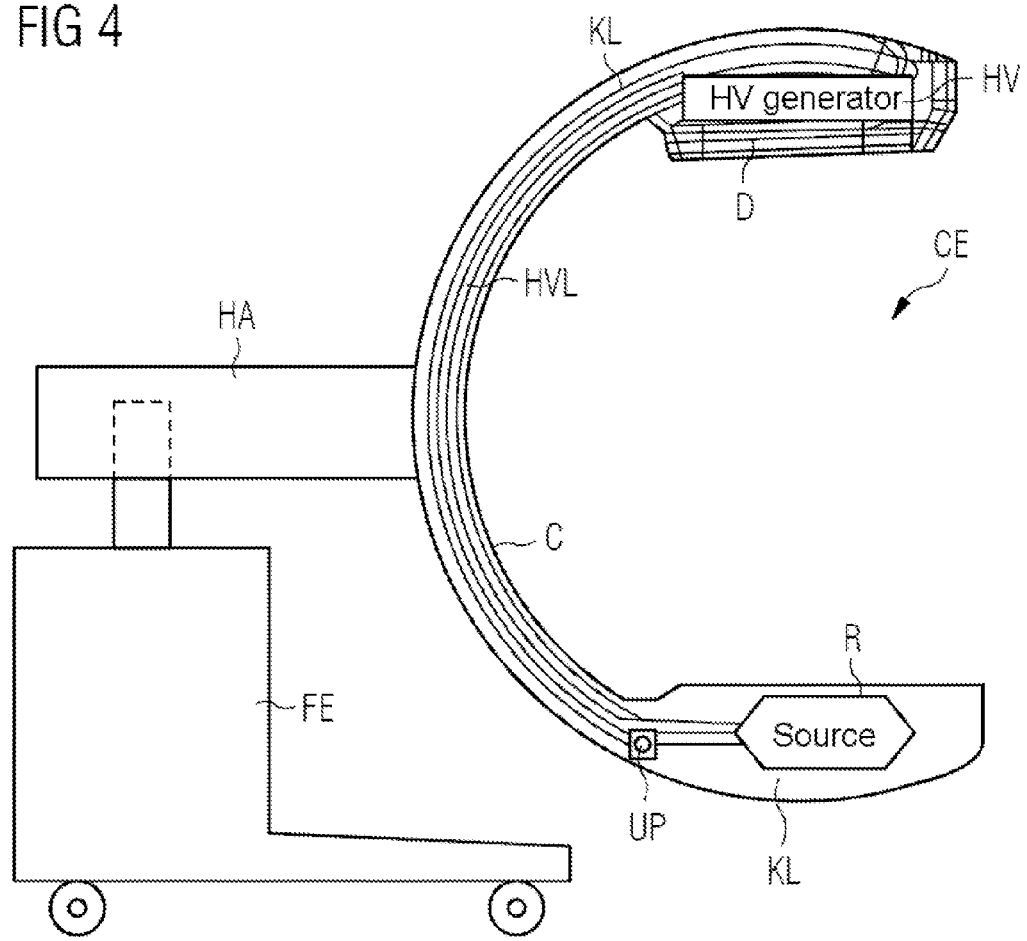

X-RAY APPARATUS WITH VOLTAGE GENERATOR COMPONENT DISPOSED AT THE SAME END OF A C-ARM AS A DETECTOR

CROSS-REFERENCE TO RELATED APPLICATION

This application claims the priority, under 35 U.S.C. §119, of German application DE 10 2014 208 345.1, filed May 5, 2014; the prior application is herewith incorporated by reference in its entirety.

BACKGROUND OF THE INVENTION

Field of the Invention

The invention relates to an x-ray apparatus having a voltage generator and an x-ray source.

X-ray technology is based on the attenuation of x-rays during transmission through an irradiated object. In this case, the central components of each x-ray device are an x-ray source and an x-ray detector which are assigned to one another in such a manner that radiation emitted by the x-ray source can be detected by the x-ray detector after passing through an x-rayed object. The source and the detector are therefore arranged opposite one another.

The arrangement of the source and the detector is typically implemented using an arm or a plurality of arms. The most common solution with an arm is the so-called C-arm, that is to say a C-shaped arm, to the two different ends of which the source and the detector are fitted. For the sake of simplicity, the topic relevant to the invention is discussed below using such a C-arm. However, the technical measures described can be applied to virtually any other desired x-ray devices.

For the use of mobile C-arms, in particular, in the clinical environment, a compact configuration and sufficient mechanical stability during rotational movements play an important role. For this reason, a corresponding weight equalization should be carried out, that is to say the masses at the ends of the C-arm should not be too different. Such a weight equalization is described in German utility model DE 694 20 936 T2, for example.

SUMMARY OF THE INVENTION

It is accordingly an object of the invention to provide an X-ray apparatus that overcomes the above-mentioned disadvantages of the prior art devices of this general type, which has an efficient weight equalization in the x-ray components.

The object is achieved by an x-ray apparatus according to the main claim.

The x-ray apparatus according to the invention having a C-arm frame (C-arm) contains a voltage generator (preferably a high-voltage generator) and an x-ray source. The voltage generator is a central part of the voltage supply. At least one component of the voltage generator and the x-ray source are arranged separately from one another in or on the x-ray apparatus, this at least one component of the voltage generator is positioned at the same end of the C-arm frame at which the detector is also arranged. This at least one component may be, for example, a voltage transformer, a voltage rectifier, a voltage capacitor, a heating transformer, a combination of these components or the entire voltage generator.

The at least one component of the voltage generator is preferably arranged in the vicinity of the detector which is provided for the purpose of recording radiation emitted by the x-ray source. In this case, "in the vicinity" is intended to be understood as meaning that, in the case of an x-ray device in which the x-ray source and the x-ray detector are fitted to the same arm (for example C-arm), the at least one component of the voltage generator is positioned at the same end of the arm as the detector. If the source and the detector are fitted to different arms, "in the vicinity" is intended to be interpreted such that the detector and the at least one component of the voltage generator are fitted to the same arm. For example, the at least one component of the voltage generator may be arranged on that side of the detector which faces away from the x-ray source (in the recording position).

The invention allows a better weight equalization by separating the comparatively heavy components of the x-ray source and (at least partially) the voltage generator.

At least one additional component which is not associated with the voltage generator or the x-ray source and is needed to supply voltage to the x-ray source (for example a starter or heating transformer) may also be arranged in the at least one component of the voltage generator. In this case, it is useful to provide components needed to supply the voltage in accordance with the best possible weight equalization for an arrangement separate from the x-ray source. Additional compensation weights for the weight equalization are then no longer required or are required only to a lesser extent. Such a weight equalization is important, in particular, for mobile x-ray devices, but may also be used for stationary systems, for example floor-mounted or ceiling-mounted systems. In order to supply voltage to the source, a high-voltage line for connecting the at least one component of the voltage generator and the x-ray source can be integrated inside the C-arm, for example.

Other features which are considered as characteristic for the invention are set forth in the appended claims.

Although the invention is illustrated and described herein as embodied in an x-ray apparatus, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 is a schematic illustration of an x-ray tube;
and
FIG. 4 is a diagrammatic, longitudinal section view through a C-arm according to the invention.

DETAILED DESCRIPTION OF THE INVENTION

Figure 1:
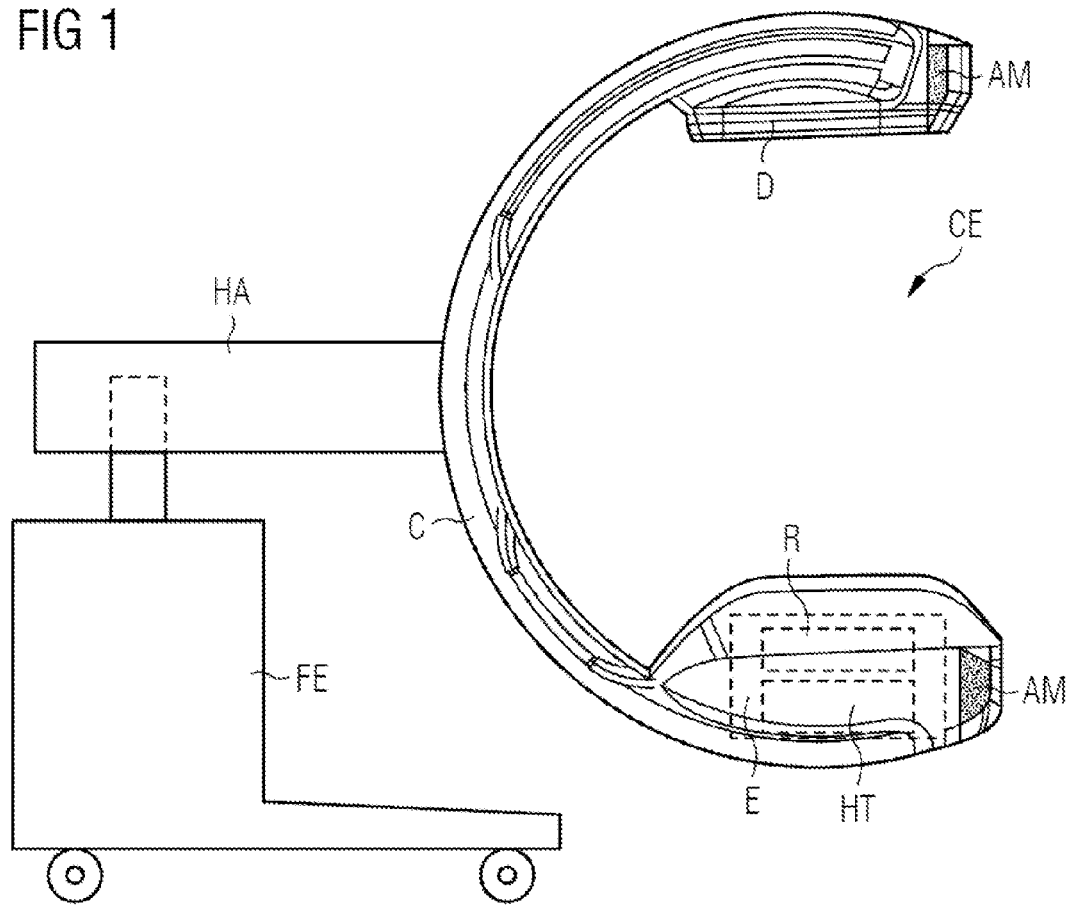
FIG. 1 is an illustration of a conventional C-arm according to the prior art.

Referring now to the figures of the drawing in detail and first to FIG. 1 thereof, there is shown a C-arm CE according to the prior art. An arm HA, to the end of which the C-arm frame CE is fastened, is fitted to a mobile unit FE—usually in such a manner that it can be rotated about a vertical axis.

A self-contained generator E having an x-ray source R and a high-voltage generator HT is arranged at the lower end of the C-arm frame CE in FIG. 1. The radiation emitted by the x-ray source R is detected by a detector D arranged at the other end of the C-arm frame. For easier positioning of the C-arm unit C, adjustment devices AM are arranged at the ends of the C-arm frame C. These adjustment devices AM are generally configured in such a manner that weight equalization with respect to the two ends is ensured.

Figure 2:
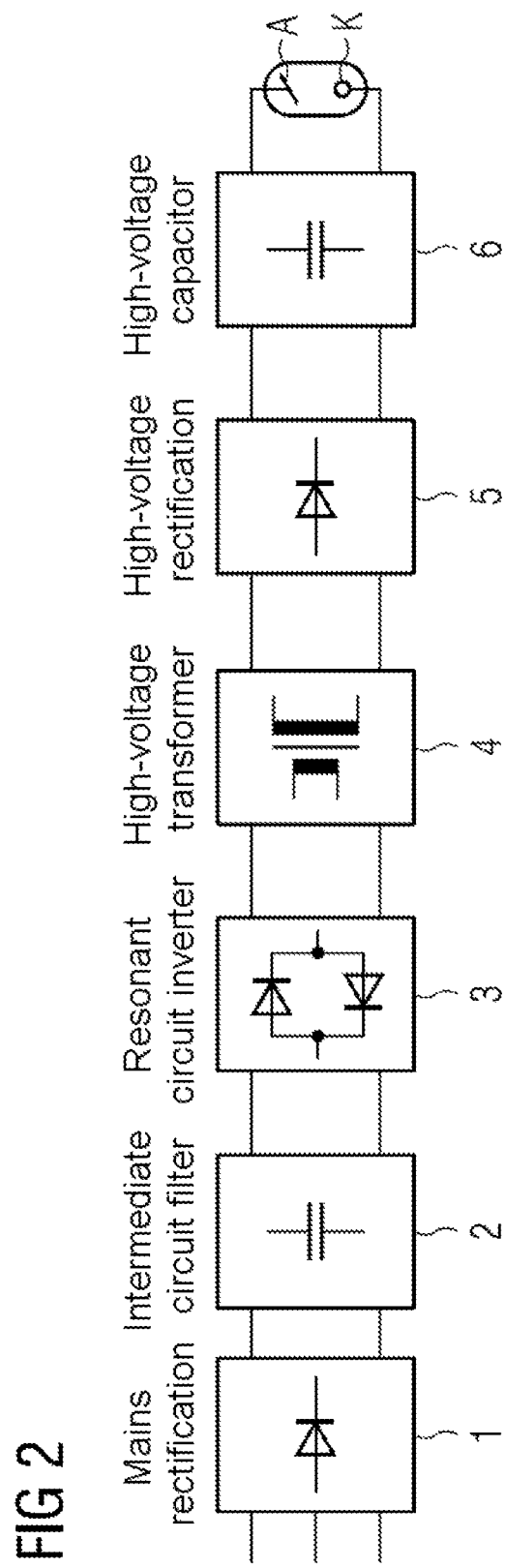
FIG. 2 is a basic circuit diagram of an x-ray generator.

The two central components of the self-contained generator E, the x-ray source R and the components for high-voltage generation HT, are described in somewhat more detail below. FIG. 2 shows a basic circuit diagram of an apparatus for generating high voltage which is provided for an x-ray device. This apparatus typically uses inverter technology. The voltage applied to the x-ray tube 7 between the anode A and the cathode K is a DC voltage. This is generated with the aid of a generator or a high-voltage transformation apparatus. The DC voltage obtained by a mains rectifier 1 and an intermediate circuit filter 2 is converted into an AC voltage using a resonant circuit inverter 3. This AC voltage is transformed, by a high-voltage transformer 4, into a high voltage which is converted into a DC voltage for the x-ray tube 7 by a high-voltage rectifier 5 and is filtered using a high-voltage capacitor 6.

FIG. 3 schematically shows an x-ray tube. A vacuum housing V is arranged in an oil bath Ö required for cooling. The vacuum housing V contains a cathode K which is heated in order to generate free electrons. These electrons are accelerated in the direction of a rotating anode A by an acceleration voltage (not illustrated in the figure). The electron beam e generated in this manner strikes the anode A. This is usually a rotating anode which is caused to rotate R for the purpose of heat dissipation. The firing of the anode material produces x-rays R which leave the vacuum housing V through an exit window F. A high voltage (for example 100 kV) is needed to operate the x-ray source.

A central consideration of the present invention is that x-rays are generated with the aid of two central components, namely a high-voltage generator and an x-ray source, which function in a relatively autonomous or independent manner and can therefore also be spatially separate. A further important observation is that the high-voltage generator and the x-ray source typically together have a comparable weight (for example 25-30 kg), whereas the detector has a considerably lower weight, often a weight lower by an order of magnitude (for example 3 kg).

This is used by the invention. The invention proposes spatially separating the main components of the self-contained generator (source/voltage generation). For example, all of the components of the so-called high-voltage generator are separated from the source. The high-voltage generator mainly contains the following components: high-voltage transformer, high-voltage rectifier, high-voltage capacitor and heating transformer. For the exemplary embodiment, it is assumed below that the high-voltage generator is arranged separately from the source and is arranged separately in its own housing. The invention is not restricted thereto. In particular, additional components which are provided for the purpose of supplying voltage may be separated from the source and may be moved to the high-voltage generator.

The voltage or HF generator is preferably arranged on the side opposite the source behind the detector (usually a flat-panel detector). This is shown in more detail in FIG. 4 for a mobile C-arm CE.

In contrast to conventional systems, the high-voltage generator HV for generating the high voltage required by the x-ray source does not form an integrated system with the source (self-contained generator), but rather is arranged separately from the source in the detector D on the side facing away from the source. The high-voltage generator HV and the source R are connected to one another by an appropriately insulated high-voltage line HVL. A cooling line system KL or cooling circuit (air or water) is provided for the purpose of cooling the components and contains, for example, a circulating pump UP for the cooling medium. The cooling line system KL is guided inside the C-arm frame C in such a manner that it reaches both ends and therefore also effects heat dissipation for the x-ray source R and the high-voltage generator HV. Alternatively, the cooling medium can also be alternatively or additionally guided through the C-arm cable into the mobile unit FE for cooling.

This arrangement has a number of now described advantages.

Weight equalization as a result of relatively similar masses at the ends is achieved. Therefore, only considerably lighter additional weights are needed, if at all, for balancing.

It is possible to increase the distance between the source and the isocenter defined by reference to the arm rotation. This becomes clear from the comparison between FIG. 1 and FIG. 4. In the C-arm according to the invention from FIG. 4, the position of the x-ray source is shifted in the opposite direction to the detector. That is to say, the C-arm can be conceptually configured in such a manner that a greater distance between the source and the isocenter results. With the same distance to the isocenter, a C-arm according to the invention can again be configured to be more compact in terms of the design than a conventional C-arm.

In conventional x-ray devices, it is necessary to replace the entire self-contained generator if one component of the self-contained generator fails. In contrast, in x-ray devices configured according to the invention, the individual components can be replaced, that is to say, in the case of a defective source, only the source needs to be replaced and not the entire self-contained generator. The service possibilities for the individual components are therefore improved.

The divided arrangement of the x-ray source and the x-ray generator according to the invention enables better cooling since the main heat source (namely the source) is insulated and the further heat sources (generator, detector) are arranged on the other side. The heat dissipation is therefore improved by skilled division of the heat sources.

The statements made above relate only to one embodiment of the subject matter of the invention which is not intended to restrict the scope of protection. A person skilled in the art arrives at further refinements without constraint as a result of routine practice. In particular, a C-arm is only one possible type of x-ray device for which the invention can be advantageously used.

The invention claimed is:

1. An x-ray apparatus, comprising:
   a C-arm frame having a middle section, a first end remote from said middle section, and a second end remote from said middle section;
   an x-ray source disposed at said first end;
   a detector for recording radiation emitted by said x-ray source and disposed at said second end; and
   a voltage generator for supplying a voltage to said x-ray source, and at least one component of said voltage generator and said x-ray source being disposed separately from one another, said at least one component of said voltage generator is disposed at said second end of said C-arm frame at which said detector is disposed;

wherein said at least one component of said voltage generator is selected from the group consisting of a voltage transformer, a voltage rectifier, a voltage capacitor, a heating transformer, a combination thereof and said voltage generator entirely.

2. The x-ray apparatus according to claim 1, wherein said at least one component of said voltage generator is disposed on that side of said detector which faces away from said x-ray source.

3. The x-ray apparatus according to claim 1, further comprising a starter or heating transformer disposed in said at least one component of said voltage generator.

4. The x-ray apparatus according to claim 1, wherein components needed to supply the voltage to said x-ray source are provided in accordance with optimized weight equalization for an arrangement separate from said x-ray source.

5. The x-ray apparatus according to claim 1, wherein the x-ray apparatus is selected from the group consisting of a mobile x-ray apparatus and a stationary x-ray apparatus.

6. The x-ray apparatus according to claim 1, further comprising a high-voltage line for connecting said at least one component of said voltage generator to said x-ray source, said high-voltage line is integrated inside said C-arm frame.

7. The x-ray apparatus according to claim 1, further comprising at least one additional compensation weight for weight equalization.

8. The x-ray apparatus according to claim 1, wherein said at least one component of said voltage generator and said x-ray source are located opposite each other.

\* \* \* \* \*